United States Patent [19]

Shepard et al.

[11] 4,006,233

[45] Feb. 1, 1977

[54] N-(PYRIMIDINYL)-TRICYCLO[3(OR 4).2.2.0$^{2,4(or\ 5)}$]-NON (OR DEC)ENEDICARBOXIMIDES

[75] Inventors: Kenneth L. Shepard, Ambler; William J. Paleveda, Jr., Lansdale, both of Pa.

[73] Assignee: Merck & Co., Inc., Rahway, N.J.

[22] Filed: May 9, 1975

[21] Appl. No.: 575,918

Related U.S. Application Data

[63] Continuation-in-part of Ser. No. 511,961, Oct. 4, 1974, abandoned.

[52] U.S. Cl. .......................... 424/251; 260/302 H; 260/307 C; 260/326 A; 260/326 HL; 260/326 N; 260/326 R; 260/256.4 N
[51] Int. Cl.$^2$ ........................................ C07D 403/04
[58] Field of Search ............ 260/256.4 N; 424/251

[56] References Cited

UNITED STATES PATENTS

| | | | |
|---|---|---|---|
| 3,126,395 | 3/1964 | Kitahonoki et al. | 260/326 C |
| 3,476,546 | 11/1969 | Roberts et al. | 260/326 C |

*Primary Examiner*—Donald G. Daus
*Assistant Examiner*—James H. Turnipseed
*Attorney, Agent, or Firm*—William H. Nicholson; James A. Arno; Harry E. Westlake, Jr.

[57] ABSTRACT

Tricyclicdicarboximides representatively prepared by the Diels-Alder condensation of a cyclic diene such as cycloheptatriene, cyclooctatetraene and the like with a dienophile such as substituted N-phenylmaleimide and the like are disclosed having pharmaceutical utility as minor tranquilizers and anti-convulsants. Also disclosed are processes for the preparation of such tricyclicdicarboximides; pharmaceutical compositions comprising such compounds and their salt, ester and amide derivatives; and methods of treatment comprising administering such compounds and compositions.

4 Claims, No Drawings

N-(PYRIMIDINYL)-TRICYCLO[3(OR 4).2.2.0$^{2,\text{-}\text{or}\,5}$]-NON (OR DEC)ENEDICARBOXIMIDES This application is a continuation-in-part of co-pending application Ser. No. 511,961, filed Oct. 4, 1974 now abandoned.

BACKGROUND OF THE INVENTION

This invention relates to certain tricyclicdicarboximides which representatively are characterized in that they are the Diels-Alder condensation products of a cyclic diene and an N-substituted maleimide. Such tricyclicdicarboximides (Structure I, below) and their pharmaceutically acceptable salt, ester and amide derivatives are useful as minor tranquilizing and anti-convulsant agents. This invention also relates to processes for the preparation of such tricyclicdicarboximides, to pharmaceutical compositions comprising such compounds, and to methods of treatment comprising administering such compounds and compositions.

Structure I, below generically depicts the compounds of the present invention which are hereinafter collectively referred to as "tricyclicdicarboximides":

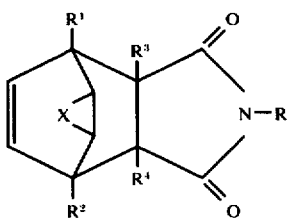

wherein:
$R^1$, $R^2$, $R^3$ and $R^4$ are selected from the group consisting of hydrogen, halogen, alkyl, aminoalkyl, carboxyalkyl, aralkyl, cycloalkyl, haloalkyl, acyloxy, alkenyl, and dialkylaminoalkyl;

X is —CH$_2$— (in which case the cyclic diene reactant necessary for the preparation of I is a bond isomer of cycloheptatriene or a substituted derivative thereof), or —CH=CH— (in which case the cyclic diene reactant necessary for the preparation of I is a bond isomer of cyclooctatetraene or a substituted derivative thereof);

R is selected from the group consisting of:
—CH$_2$C=CH

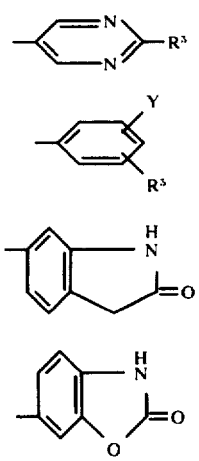

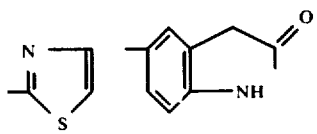

wherein Y is hydrogen, halogen, lower alkyl, aminoalkyl, carboxyalkyl, alkoxy, carbalkoxy, carbamoyl and haloalkyl; and $R^5$ is acylamino, and amino.

Thus, it is an object of the present invention to provide tricyclicdicarboximides of the above general description (I). It is also an object of this invention to provide pharmaceutical compositions comprising such tricyclicdicarboximides and their non-toxic, pharmaceutically acceptable salt, ester and amide derivatives. Lastly, it is an object of the present invention to provide methods of treatment comprising administering the compounds and compositions of the present invention in situations where a minor tranquilizer is indicated.

DETAILED DESCRIPTION OF THE INVENTION

The tricyclicdicarboximides of the present invention are most conveniently prepared by the Diels-Alder condensation of a polycyclic diene (i.e., as previously indicated the bond isomer of cycloheptatriene or cyclooctatraene) and an N-substituted maleimide:

REACTION I

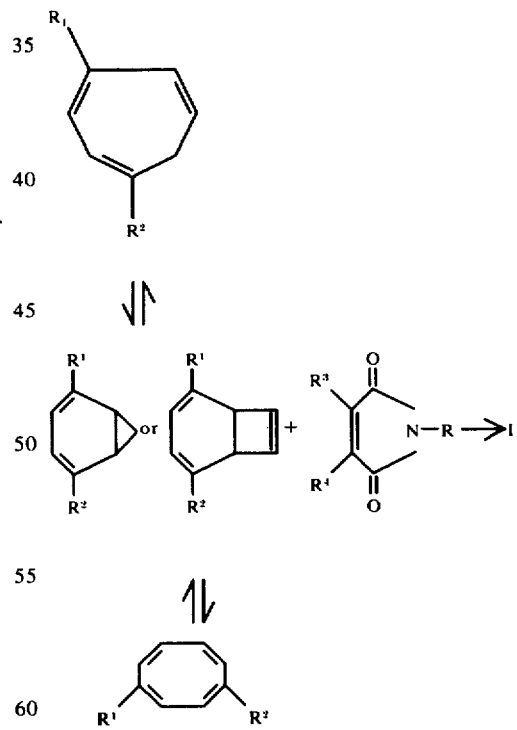

wherein all substituents have previously been defined.

Alternately the tricyclicdicarboximides of the present invention may be prepared by reacting a substituted amino compound, H$_2$N—R, with the Diels-Alder product obtained by reacting either cycloheptatriene (or substituted derivatives thereof) or cyclooctatetraene (or substituted derivatives thereof) with maleic anhydride.

REACTION II

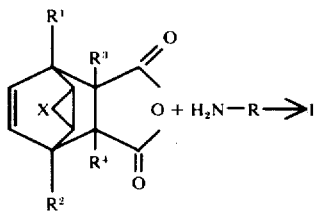

wherein all substituents are as previously defined.

In Reaction I (above) the reaction is preferably carried out in a solvent such as pyridine, glyme, toluene, xylene and the like at a temperature in the range of from about 0° C. to the reflux temperature. However, there is no undue criticality as to the identity of the reaction solvent and reaction temperature. In Reaction II the reaction solvent is preferably pyridine, benzene, 2-propanol and the like and the reaction temperature is in the range of from about 0° C. to the reflux temperature. However, there is no undue criticality as to the condition of reaction. The Diels-Alder reactant in Reaction II is prepared by conventional procedures such as by contacting the dienophile (e.g. maleic anhydride) with an excess of the diene (cyclooctatraene or cycloheptatriene) at a temperature of from about 0° C. to about 200° C.; alternately a solvent such as benzene, toluene, xylene and the like may be used at a temperature of from about 0° C. to about 200° C.

The tricyclicdicarboximide (I) resulting from either Reaction I or Reaction II is predominately in the endo configuration, and this form is preferred for practice of the present invention.

Non-toxic pharmaceutically acceptable salt, ester and amide derivatives of the tricyclicdicarboximides of the present invention are prepared by conventional procedures. Preferred N-addition salts are those such as derived from hydrochloric acid, hydrobromic acid, and the like. For those embodiments of I which possess a carboxylic acid group preferred salts are those obtained from the alkali and alkaline earth metals; suitable amides are those obtained from bases such as methylamine, N,N-dimethylethylenediamine and the like; suitable esters may be prepared by conventional means from the free acid form of I, and may, for example, be selected from the group consisting of methyl, ethyl and the like.

The preferred tricyclicdicarboximides of the present invention are those wherein $R^1$, $R^2$, $R^3$, and $R^4$ are hydrogen; and X and R are as previously defined.

In the method of treatment aspect of the present invention, the instant minor tranquilizer tricyclicdicarbodicarboximides are capable of producing anxiety relief without causing excessive sedation or sleep at a unit dosage level of from about 0.001 to about 8.00 mg. per kg. of body weight, or at a daily dosage level of from about 0.004 to about 32.00 mg. per kg. of body weight. Of course, it is understood that the exact treatment level will depend upon the case history of the animal or human individual being treated and in the last analysis the precise treatment level falling within the above guidelines is at the routine discretion of the therapist.

Also included within the scope of the present invention are pharmaceutical compositions comprising such tricyclicdicarboximides. Preferably these compositions are in unit dosage forms such as tablets, pills, capsules, powders, granules, sterile parenteral solutions or suspensions, and the like. For preparing solid compositions such as tablets, the principal active ingredient is mixed with a pharmaceutical carrier, i.e., conventional tableting ingredients such as corn starch, lactose, sucrose, sorbitol, talc, stearic acid, magnesium stearate, dicalcium phosphate, gums, and other pharmaceutical diluents, e.g., water, to form a solid preformulation composition containing a homogeneous mixture of a tricyclicdicarboximide of the present invention, or a non-toxic pharmaceutically acceptable salt, ester or amide derivative thereof. When referring to these preformulation compositions as homogeneous, it is meant that the active ingredient, i.e., the tricyclicdicarboximide, is dispersed evenly throughout the composition so that the composition may be readily subdivided into equally effective unit dosage forms such as tablets, pills, capsules, and the like. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action of the instant tricyclicdicarboximide. For example, the tablet or pill can comprise an inner dosage and an outer dosage component, the latter being in the form of an envelope over the former. The two components can be separated by an enteric layer which serves to resist disintegration in the stomach and permits the inner component to pass intact into duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like.

The liquid forms in which the novel composition of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, gelatin and the like.

The pharmaceutical tricyclicdicarboximide formulations of the present invention can be administered orally, parenterally, or rectally. Orally, they may be administered in tablets, capsules, suspensions or syrups, the preferred dosage form being a compressed tablet containing from 0.1 to about 500 mg. of the active ingredient. The optimum dosage depends of course on the dosage form being used and the type and severity of the condition being treated. In any specific case, as previously mentioned, the appropriate dosage selected will further depend on factors of the patient which may influence response to the drug, for example, general health, age, weight, and the desired effect.

The following Examples representatively illustrate, but do not limit, the product, process, method of treatment, or compositional aspects of the present invention.

EXAMPLE 1

N-(4-Acetamidophenyl)-anti-tricyclo[3.2.2.0$^{2,4}$]-non-8-ene-endo-6,endo-7-dicarboximide

Method I

A mixture of N-(4-acetamidophenyl)maleimide (1.61 g., 0.007 mole), 1,3,5-cycloheptatriene (0.64 g., 0.007 mole), and xylene (50 ml.) is refluxed for 22 hours. The resulting hot yellow solution is decanted from a gummy precipitate and cooled. The yellow solid that separates is collected and air-dried, 1.57 g., (70%). Recrystallization from isopropyl alcohol yields N-(4-acetamidophenyl)-anti-tricyclo[3.2.2.0$^{2,4}$]non-8-ene-endo-6,endo-7-dicarboximide, m.p. 229–231.

Analysis Calc. for: $C_{19}H_{18}N_2O_3$: Calc.: C, 70.79; H, 5.63; N, 8.69. Found: C, 70.92; H, 6.00; N, 8.78.

Method II

A mixture of anti-tricyclo[3.2.2.0$^{2,4}$]non-8-ene-endo-6,endo-7-dicarboxylic anhydride (4.11 g., 0.022 mole), 4'-aminoacetanilide (9.73 g., 0.065 mole), and pyridine (28 ml.) is heated under reflux for 18 hours. The solvent is removed at 25° C., water (50 ml.) is added and the mixture is acidified by the addition of concentrated hydrochloric acid (15 ml.). The solid that separates is collected, washed with water, 0.1N, hydrochloric acid, water and dried to constant weight, 6.66 g. (96%), m.p. 229°–231° C. Repeated recrystallization from ethanol gives N-(4-acetamidophenyl)-anti-tricyclo[3.2.2.0$^{2,4}$]non-8-ene-endo-6,endo-7-dicarboximide, m.p. 230°–231.5° C.

Analysis Calc. for: $C_{19}H_{18}N_2O_3$: Calc.: C, 70.79; H, 5.63; N, 8.69. Found: C, 71.09; H, 5.54; N, 8.68.

EXAMPLE 2

N-(4-Acetamidophenyl)-anti-tricyclo[4.2.2.0$^{2,5}$]dec-3,9-diene-endo-7,endo-8-dicarboximide A mixture of tricyclo[4.2.2.0$^{2,5}$]dec-3,9-diene-endo-7,endo-8-dicarboxylic anhydride (2.02 g., 0.01 mole), 4'-aminoacetanilide (1.50 g., 0.01 mole), and pyridine (20 ml.) is refluxed for 20 hours. The pyridine is removed "in vacuo" to yield the product as a tan solid, 3.05 g. (0.0091 mole, 91% yield), m.p. 225°–236° C. Two recrystallizations from isopropyl alcohol yields N-(4-acetamidophenyl)-anti-tricyclo[4.2.2.0$^{2,5}$]dec-3,9-diene-endo-7,endo-8-dicarboximide as an off-white solid, 1.65 g., m.p. 223°–235° C.

Analysis Calc. for: $C_{20}H_{18}N_2O_3$: Calc.: C, 71.84; H, 5.43; N, 8.38. Found: C, 72.01; H, 5.61; N, 8.21.

EXAMPLE 3

N-(3-Acetamidophenyl)-anti-tricyclo[4.2.2.0$^{2,5}$]dec-3,9-diene-endo-7,endo-8-dicarboximide A mixture of tricyclo[4.2.2.0$^{2,5}$]dec-3,9-diene-endo-7,endo-8-dicarboxylic anhydride (2.02 g., 0.01 mole), 3'-aminoacetanilide (1.50 g., 0.01 mole), and pyridine (20 ml.) is refluxed for 24 hours. The pyridine is removed in vacuo to yield the product as a tan solid, 3.20 g. (0.00955 mole, 95.5% yield), m.p. 260°–265° C. Recrystallization from acetonitrile yields N-(3-acetamidophenyl)-anti-tricyclo[4.2.2.0$^{2,5}$]dec-3,9-diene-endo-7,endo-8-dicarboximide as an off-white solid, 2.0 g., m.p. 264°–266° C.

Analysis Calc. for $C_{20}H_{18}N_2O_3$: Calc.: C, 71.84; H, 5.43; N, 8.38. Found: C, 71.92; H, 5.66; N, 8.52.

EXAMPLE 4

N-(6-Benzoxazolinyl-2-one)-anti-tricyclo[4.2.2.0$^{2,5}$]-dec-3,9-diene-endo-7,endo-8-dicarboximide A mixture of anti-tricyclo[4.2.2.0$^{2,5}$]dec-3,9-diene-endo-7,endo-8-dicarboxylic anhydride (0.67 g., 0.0033 mole), 6-aminobenzoxazolin-2-one (0.49 g., 0.0033 mole) and pyridine (10 ml.) is heated under reflux for 16 hours. The reaction mixture is cooled (25° C.), diluted with water (100 ml.) and the solid that separates is collected and dried, 0.95 g. Recrystallization from ethanol gives N-(6-benzoxazolinyl-2-one)-anti-tricyclo[4.2.2.0$^{2,5}$]-dec-3,9-diene-endo-7,endo-8-dicarboximide, m.p. 306°–309° C.

Analysis Calc. for: $C_{19}H_{14}N_2O_4$: Calc.: C, 68.25; H, 4.22; N, 8.38. Found: C, 68.35; H, 4.41; N, 8.33.

EXAMPLE 5

N-(6-Benzoxazolinyl-2-one)-anti-tricyclo[3.2.2.0$^{2,4}$]-non-8-ene -endo-6,endo-7-dicarboximide Following the procedure of Example 4 and using anti-tricyclo[3.2.2.0$^{2,4}$]non-8-ene-endo-6,-endo-7-dicarboxylic anhydride (0.95 g., 0.005 mole), 6-aminobenzoxazolin-2-one (0.75 g., 0.005 mole) and pyridine (10 ml.) there is obtained 1.45 g., of solid, m.p. 265.5°–267° C (dec.). Recrystallization from 2-propanol provides N-(6-benzoxazolinyl-2-one)-anti-tricyclo[3.2.2.0$^{2,4}$]non-8-ene-endo-6,-endo-7-dicarboximide, m.p. 283°–284.5° C. (dec.).

Analysis Calc. for: $C_{18}H_{14}N_2O_4$: Calc.: C, 68.25; H, 4.22; N, 8.38. Found: C, 68.33; H, 4.31; N, 8.34.

EXAMPLE 6

N-(5-Benzoxazolinyl-2-one)-anti-tricyclo[4.2.2.0$^{2,5}$]-dec-3,9-diene-endo-7,endo-8-dicarboximide A mixture of anti-tricyclo[4.2.2.0$^{2,5}$]dec-3,9-diene-endo-7,endo-8-dicarboxylic anhydride (2.02 g., 0.01 mole), 5-aminobenzoxazolin-2-one (1.50 g., 0.01 mole) and pyridine (20 ml.) is heated under reflux for six hours. The cooled solution (25° C.) is diluted with water (200 ml.) and the precipitate is collected by filtration, 2.60 g., m.p. 252°–257° C. Recrystallization from 2-propanol provides N-(5-benzoxazolinyl-2-one)-anti-tricyclo[4.2.2.0$^{2,5}$]dec-3,9-diene-endo-7,endo-8-dicarboximide, m.p. 287.5°–290° C.

Analysis Calc. for $C_{19}H_{14}N_2O_4$: Calc.: C, 68.25; H, 4.22; N, 8.38. Found: C, 68.33; H, 4.31; N, 8.34.

EXAMPLE 7

N-(5-Benzoxazolinyl-2-one)-anti-tricyclo[3.2.2.0$^{2,4}$]-non-8-ene-endo -6,endo-7-dicarboximide Following the procedure of Example 6 and using anti-tricyclo[3.2.2.0$^{2,4}$]non-8-ene-endo-6,endo-7-dicarboxylic anhydride (1.90 g., 0.01 mole), 5-aminobenzoxazolin-2-one (1.5- g., 0.01 mole) and pyridine (20 ml.), there is obtained 2.65 g. of yellowish solid, m.p. 252°–257° C. (dec. with eff.). Recrystallization from 2-propanol give N-(5-benzoxazolinyl-2-one)-anti-tricyclo[3.2.2.0$^{2,4}$]non-8ene-endo-6,endo-7-dicarboximide, m.p. 256°–258° C.

Analysis Calc. for $C_{18}H_{14}N_2O_4$: Calc.: C, 67.07; H, 4.38; N, 8.69. Found: C, 67.05; H, 4.49; N, 8.63.

EXAMPLE 8

N-(2-Acetamido-5-pyrimidinyl)-anti-tricyclo[4.2.2.0$^{2,5}$]dec-3,9-diene-endo-7,endo-8-dicarboximide A mixture of anti-tricyclo[4.2.2.0$^{2,5}$]dec-3,9-diene-endo-7,endo-8-dicarboxylic anhydride (1,21 g., 0.006 mole), 2-acetamido-5-aminopyrimidine (0.92 g., 0.006 mole), and pyridine (20 ml.) is heated under reflux for 24 hours. The pyridine is removed in vacuo to yield, after washing with water, 2.0 g. (0.006 mole, 100% yield), m.p. 232°–245° C. Two recrystallizations from isopropyl alcohol produces N-(2-acetamido-5-pyrimidinyl)-anti-tricyclo[4.2.2.0$^{2,5}$]-dec-3,9-diene-endo-7,endo-8-dicarboximide as a white crystalline solid, 1.14 g., m.p. 246.5°–249.5° C.

Analysis Calc. for: $C_{18}H_{16}N_4O_3$: Calc.: C, 64.27; H, 4.80; N, 16.66. Found: C, 64.21, H, 4.79; N, 16.56.

EXAMPLE 9

N-(Propargyl)-anti-tricyclo[3.2.2.0$^{2,4}$]non-8-ene-endo-6,-endo-7-dicarboximide A mixture of anti-tricyclo[3.2.2.0$^{2,4}$]non-8-ene-endo-6,endo-7-dicarboxylic anhydride (5.70 g., 0.03 mole), mono-propargylamine hydrochloride (2.76 g., 0.03 mole), and pyridine (60 ml.) is heated under reflux for six hours. The pyridine is removed in vacuo, and the residue triturated with water (50 ml.) to yield 6.5 g. (0.028 mole, 93%) of the crude product. Recrystallization from hexane produce N-(propargyl)-anti-tricyclo[3.2.2.0$^{2,4}$]-non-8-ene-endo-6,-endo-7-dicarboximide as a white crystalline solid, 5.1 g., m.p. 108°–110° C.

Analysis Calc. for $C_{14}H_{13}NO_2$: Calc: C, 73.99; H, 5.77; N, 6.16. Found: C, 73.90; H, 6.09; N, 6.30.

EXAMPLE 10

N-(3-Chloro-4-valeramidophenyl-anti-tricyclo[4.2.2.0$^{2,5}$]-dec-3,9-diene-endo-7,endo-8-dicarboximide Step A: 2'-Chloro-4'-nitrovaleranilide Valeryl chloride (12.06 g., 0.10 mole) is added dropwise to a cooled stirred solution of 2-chloro-4-nitroaniline (17.26 g., 0.10 mole) in pyridine (100 ml.). The mixture is warmed to ambient temperature, then heated (80°–100° C.) for 24 hours. The cooled solution is poured into cold 1 N hydrochloric acid (500 ml.) with stirring. The precipitated solid is collected, washed well with water and dried, 25.1 g., m.p. 80°–95° C. Recrystallization from cyclohexane yeilds material (19.75 g.) of m.p. 95°–97° C.

Step B: 4'-Amino-2'-chlorovaleranilide

2'-Chloro-4'nitrovaleranilide (13.0 g.) is dissolved in warm glacial acetic acid (100 ml.) and iron powder (14 g.) is added portionwise to maintain gentle boiling. The resulting reaction mixture is refluxed for one-half hour and filtered. The filtrate is evaporated under reduced pressure and the residue is triturated with water. The solid that forms is collected (11.5 g.) and recrystallized from cyclohexane to yield 7.5 g., m.p. 96.5°–99° C.

Step C: N-(3-Chloro-4-valeramidophenyl)-anti-tricylo[4.2.2.0$^{2,5}$]dec-3,9-diene-endo-7,endo-8-dicarboximide A mixture of 4'-amino-2'-chlorovaleranilide (2.27 g., 0.01 mole) anti-tricyclo[4.2.2.0$^{2,5}$]dec-3,9-diene-endo-7,endo-8-dicarboxylic anhydride (2.02 g., 0.01 mole) and pyridine (20 ml.) is heated under reflux for twenty-four hours. The solvent is removed in vacuo and the residue (4.35 g., m.p. 120°–136° C.) is recrystallized from butyl chloride to give N-(3-chloro-4-valeramidophenyl)-anti-tricyclo [4.2.2.0$^{2,5}$]dec-3,9-diene-endo-7,endo-8-dicarboximide, m.p. 157.5°–159° C.

Analysis calc. for: $C_{23}H_{23}ClN_2O_3$: Calc.: C, 67.23; H, 5.64; N, 6.82. Found: C, 67.16; H, 5.45; N, 6.87.

EXAMPLE 11

N-(4-Valeramidophenyl)-anti-tricyclo[4.2.2.0$^{2,5}$]dec-3,9-diene-endo-7,endo-8-dicarboximide Step A: 4'-Nitrovaleranilide Valeryl chloride (12.06 g., 0.10 mole) is added dropwise to a cooled stirred solution of 4-nitroaniline (13.81 g., 0.10 mole) in pyridine (100 ml.). The resulting mixture is stirred at ambient temperature for one hour then heated (80°–100° C.) for twenty-four hours. The cooled solution is poured into cold 1 N hydrochloric acid (500 ml.) with stirring. The precipitated solid is collected, washed with water and dried, 21.4 g., m.p. 107°–116° C. Recrystallization from butyl chloride provides material of m.p. 115°–118° C.

Step B: 4'-Aminovaleranilide

A solution of 4'-nitrovaleranilide (13.33 g., 0.06 mole) in absolute ethanol (750 ml.) is hydrogenated over 10% palladium on charcoal (2 g.) until the theoretical absorption is achieved. The catalyst is removed and the solvent is removed in vacuo. The residue is recrystallized from butyl chloride to yield 9.0 g., m.p. 81°–83° C.

Step C: N-(4-Valeramidophenyl)-anti-tricyclo[4.2.2.0$^{2,5}$]dec-3,9-diene-endo-7,endo-8-dicarboximide A mixture of 4'-aminovaleranilide (1.92 g., 0.01 mole), anti-tricyclo-[4.2.2.0$^{2,5}$]dec-3,9-diene-endo-7,endo-8-dicarboxylic anhydride (2.02 g., 0.01 mole) and pyridine (25 ml.) is heated under reflux for 24 hours. The solvent is removed in vacuo and the residue, 3.75 g. m.p. 214°–218° C., is recrystallized from butyl chloride to give N-(4-valeramidophenyl)-anti-tricyclo[4.2.2.0$^{2,5}$]dec-3,9-diene-endo-7,endo-8-dicarboximide, 2.8 g., m.p. 219°–220° C.

Analysis calc. for: $C_{23}H_{24}N_2O_3$: Calc.: C, 73.38; H, 6.43; N, 7.44. Found: C, 73.41; H, 6.54; N, 7.45.

EXAMPLE 12

N-(2-Thiazolyl)-anti-tricyclo[3.2.2.0$^{2,4}$]non-8-ene-endo-6,endo-7-dicarboximide A mixture of tricyclo[3.2.2.0$^{2,4}$]non-8-ene-endo-6,endo-7dicarboxylic anhydride (1.90 g., 0.010 mole), 2-aminothiazole (1.0 g., 0.010 mole) and pyridine (20 ml.) is refluxed for 24 hours. The cooled solution is diluted with water (200 ml.) and the solid that separates is collected, washed well with water, and dried, 2.12 g. Recrystallization from butyl chloride yields N-(2-thiazolyl)-anti-tricyclo[3.2.2.0$^{2,4}$]-non-8-ene-endo-6,endo-7-dicarboximide, m.p. 154°–156° C.

Analysis calc. for: $C_{14}H_{12}N_2O_2S$: Calc.: C, 61.74; H, 4.44; N, 10.29. Found: C, 61.88; H, 4.44; N, 10.28.

EXAMPLE 13

N-(4-Aminophenyl)-anti-tricyclo[4.2.2.0$^{2,5}$]dec-3,9-diene-endo-7,endo-8-dicarboximide A mixture of N-(4-acetamidophenyl)-anti-tricyclo-[4.2.2.0$^{2,5}$]dec-3,9-diene-endo-7,endo-8-dicarboximide (0.90 g.), benzylamine (1 ml.) and methyl cellosolve (10 ml.) is heated under reflux for 18 hours. Benzylamine (1 ml.) is added and heating is continued for an additional 24 hours. The solvent is removed in vacuo, butyl chloride is added and the solid that separates is collected, 0.65 g. Recrystallization from 95% ethanol gives N-(4-aminophenyl)-anti-tricyclo-[4.2.2.0$^{2,5}$]dec-3,9-diene-endo-7,endo-8dicarboximide, m.p. 321°–324° C. (dec.).

Analysis calc. for: $C_{18}H_{16}N_2O_2$: Calc. C, 73.95; H, 5.52; N, 9.58. Found: C, 73.04; H, 5.74; N, 9.50.

EXAMPLE 14

N-(5-Indolinyl-2-one)-anti-tricyclo[4.2.2.0$^{2,5}$]dec-3,9-diene-endo-7,endo-8-dicarboximide A mixture of anti-tricyclo[4.2.2.0$^{2,5}$]dec-3,9-diene-endo-7, endo-8-dicarboxylic anhydride (2.02 g., 0.010 mole), 5-aminoindolin-2-one (1.48 g., 0.01 mole) and pyridine (20 ml.) is heated under reflux for 20 hours. The cooled reaction mixture is diluted with water (200 ml.) and the solid that separates is collected, washed with water, and dried, 2.50 g. Recrystallization from 2-propanol yields N-5-indolinyl-2-one)-anti-tricyclo [4.2.2.0$^{2,5}$]dec-3,9-diene-endo-7, endo-8-dicarboximide, m.p. 279°–283° C.

Analysis Calc. for: $C_{20}H_{16}N_2O_3$. Calc.: C, 72.28; H, 4.85; N, 8.43. Found: C, 72.08; H, 5.03; N, 8.26.

EXAMPLE 15

N-(3-Acetamidophenyl)-anti-tricyclo[3.2.2.0$^{2,4}$]non-8-ene-endo-6,endo-7-dicarboximide A mixture of anti-tricyclo[3.2.2.0$^{2,4}$]non-8-ene-endo-6,endo-7-dicarboxylic anhydride (1.90 g., 0.01 mole), 3'-aminoacetanilide (1.50 g., 0.010 mole) and pyridine (20 ml.) is heated under reflux for 24 hours. The solvent is removed in vacuo and the residue is recrystallized from 2-propanol to give N-(3-acetamidophenyl)-anti-tricyclo[3.2.2.0$^{2,4}$]non-8-ene-endo-6,endo-7-dicarboximide, 1.85 g., m.p. 251.5°–252.5° C.

Analysis Calc. for: $C_{19}H_{18}N_2O_3$: Calc.: C, 70.79; H, 5.63; N, 8.69. Found: C, 70.63; H, 5.77; N, 8.47.

EXAMPLE 16

N-(3-Aminophenyl)-anti-tricyclo[3.2.2.0$^{2,4}$]non-8-ene-endo-6,endo-7-dicarboximide A mixture of anti-tricyclo[3.2.2.0$^{2,4}$]non-8-ene-endo-6,endo-7-dicarboxylic anhydride (0.95 g., 0.0005 mole), 1-(3-aminophenyl)urea hydrochloride (0.94 g., 0.005 mole), and pyridine (30 ml.) is heated under reflux for 24 hours. The cooled reaction mixture is diluted with water (200 ml.) and the solid that forms is collected and dried, 1.0 g., m.p. 204°–210° C. Recrystallization from butyl chloride yields N-(3-aminophenyl)-anti-tricyclo[3.2.2.0$^{2,4}$]non-8-ene-endo-6,endo-7-dicarboximide as a white solid, m.p. 212°–214° C.

Analysis calc. for: $C_{17}H_{16}N_2O_2$: Calc.: C, 72.84; H, 5.75; N, 9.99. Found: C, 72.71; H, 5.90; N, 9.72.

EXAMPLE 17

N-(4-Propionamidophenyl)-anti-tricyclo[4.2.2.0$^{2,5}$]-dec-3,9-diene-endo-7,endo-8-dicarboximide A mixture of anti-tricyclo[4.2.2.0$^{2,5}$]dec-3,9-diene-endo-7,endo-8-dicarboxylic anhydride (2.02 g., 0.01 mole), 4'-aminopropionanilide (1.64 g., 0.01 mole) and pyridine (20 ml.) is heated to reflux for 24 hours. The cooled reaction mixture is diluted with water (350 ml.) and the solid that separates is collected and dried, 3.4 g., m.p. 218°–221.5° C. Recrystallization from benzene gives N-(4-propionamidophenyl)-anti-tricyclo[4.2.2.0$^{2,5}$]dec-3,9-diene-endo-7,endo-8-dicarboximide with m.p. 223°–224° C.

Analysis calc. for: $C_{21}H_{20}N_2O_3$: Calc.: C, 72.39; H, 5.79; N, 8.04. Found: C, 71.38; H, 5.70; N, 7.92.

EXAMPLE 18

N-(4-Acetamido-3-chlorophenyl)-anti-tricyclo[4.2.2.0$^{2,5}$]dec-3,9-diene-endo-7,endo-8-dicarboximide A mixture of 4'-amino-2'-chloroacetanilide (0.92 g., 0.005 mole), anti-tricyclo[4.2.2.0$^{2,5}$]dec-3,9-diene-endo-7,endo-8-dicarboxylic anhydride (1.01 g., 0.005 mole) and pyridine (20 ml.) is heated under reflux for twenty hours. The cooled solution is diluted with water (200 ml.) and the solid that forms is collected and dried, 1.4 g., m.p. 195°–207° C. Recrystallization from butyl chloride gives N-(4-acetamido-3-chlorophenyl)-anti-tricyclo[4.2.2.0$^{2,5}$]-dec-3,9-diene-endo-7,endo-8-dicarboximide (0.75 g.) with m.p 207°–208° C.

Analysis calc. for: $C_{20}H_{17}ClN_2O_3$: Calc.: C, 65.13; H, 4.65; N, 7.60. Found: C, 65.22; H, 4.64; N, 7.72.

EXAMPLE 19

Tablet Preparation

Tablets containing 1.0, 2.0, 25.0, 26.0, 50.0 and 100.0 mg., respectively of N-(4-acetamidophenyl)-anti-tricyclo[3.2.2.0$^{2,4}$]non-8-ene-endo-6,endo-7-dicarboximide are prepared as illustrated below.

TABLE FOR DOSES CONTAINING FROM 1–25 MG. OF THE TRICYCLICDICARBOXIMIDE COMPOUND

|  | Amount - mg. | | |
| --- | --- | --- | --- |
| N-(4-Acetamidophenyl)-anti-tricyclo[3.2.2.0$^{2,4}$]non-8-ene-endo-6,endo-7-dicarboximide | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

TABLE FOR DOSES CONTAINING FROM 26–100 MG. OF THE TRICYCLICDICARBOXIMIDE COMPOUND

|  | Amount - mg. |
| --- | --- |
| N-(4-Acetamidophenyl)-anti-tricyclo[3.2.2.0$^{2,4}$]non-8-ene- | |

-continued

|  | Amount - mg. | | |
|---|---|---|---|
| endo-6,endo-7-dicarboximide | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | .39 | 0.75 | 1.5 |

All of the N-(4-acetamidophenyl)-anti-tricyclo-[3.2.2.0$^{2,4}$]non-8-ene-endo-6,endo-7-dicarboximide, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg., 2.0 mg., 25.0 mg., 26.0 mg., 50.0 mg., and 100.0 mg. of N-(4-acetamidophenyl)-anti-tricyclo[3.2.2.0$^{2,4}$]-non-8-ene-endo-6,endo-7-dicarboximide per tablet.

Following the procedure of Example 19, tablets comprising N-(propargyl)-anti-tricyclo[3.2.2.0$^{2,4}$]non-8-ene-endo-6,endo-7-dicarboximide are prepared when the N-(4-acetamidophenyl)-anti-tricyclo[3.2.2.0$^{2,4}$]non-8-ene-endo-6,endo-7-dicarboximide of Example 19 is replaced by an equivalent amount of N-(propargyl)-anti-tricyclo-[3.2.2.0$^{2,4}$]non-8-ene-endo-6,endo-7-dicarboximide. Other tablets are prepared using the same procedures and the equivalent amounts of excipients along with equivalent amounts of the tricyclicdicarboximide compounds of the present invention prepared in accordance with the procedures of Examples 1–18 inclusive.

What is claimed is:

1. A compound having the formula:

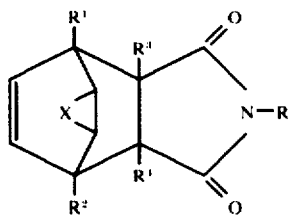

wherein:
R$^1$, R$^2$, R$^3$ and R$^4$ are hydrogen;
X is —CH$_2$— or —CH=CH—;
R is

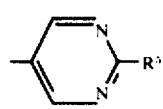

wherein R$^5$ is acetamido, or amino; or a non-toxic pharmaceutically acceptable salt thereof.

2. N-(2-acetamido-5-pyrimidinyl)-anti-tricyclo-[4.2.2.0$^{2,5}$]dec-3,9-diene-endo-7,endo-8-dicarboximide.

3. A pharmaceutical composition for the treatment of anxiety comprising a pharmaceutical carrier and a therapeutically effective amount in unitary dosage form of a compound having the formula:

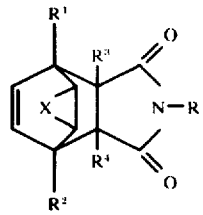

wherein:
R$^1$, R$^2$, R$^3$ and R$^4$ are hydrogen;
X is —CH$_2$— or —CH=CH—;
R is

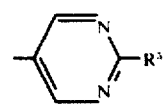

wherein R$^5$ is acetamido, or amino; or a non-toxic pharmaceutically acceptable salt thereof and a pharmaceutical carrier therefor.

4. A method of treating anxiety comprising administering to a patient in need of such treatment a therapeutically effective amount of a compound having the formula:

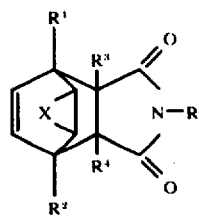

wherein
R$^1$, R$^2$, R$^3$, and R$^4$ are hydrogen;
X is —CH$_2$— or —CH=CH—;
R is

wherein R$^5$ is acetamido, and amino; or a non-toxic pharmaceutically acceptable salt thereof.

* * * * *